United States Patent
Feng et al.

(10) Patent No.: US 10,391,063 B2
(45) Date of Patent: Aug. 27, 2019

(54) PHARMACEUTICAL COMPOSITION OF POLYETHYLENE GLYCOL-MODIFIED CAMPTOTHECIN DERIVATIVE AND PREPARATION METHOD THEREOF

(71) Applicant: JenKem Technology Co., Ltd. (Tianjin), Tianjin (CN)

(72) Inventors: Zewang Feng, Tianjin (CN); Wen Li, Tianjin (CN); Zhenguo Wang, Tianjin (CN); Xuan Zhao, Tianjin (CN)

(73) Assignee: JENKEM TECHNOLOGY CO., LTD. (TIANJIN), Tainjin (CN)

( * ) Notice: Subject to any disclaimer, the term of this patent is extended or adjusted under 35 U.S.C. 154(b) by 50 days.

(21) Appl. No.: 15/613,097

(22) Filed: Jun. 2, 2017

(65) Prior Publication Data

US 2017/0266305 A1    Sep. 21, 2017

Related U.S. Application Data

(63) Continuation of application No. PCT/CN2015/096151, filed on Dec. 1, 2015.

(30) Foreign Application Priority Data

Dec. 5, 2014  (CN) .......................... 2014 1 0739978

(51) Int. Cl.
| | | |
|---|---|---|
| *A61K 9/19* | (2006.01) | |
| *A61K 9/08* | (2006.01) | |
| *A61K 9/00* | (2006.01) | |
| *A61K 9/16* | (2006.01) | |
| *A61K 47/60* | (2017.01) | |
| *A61K 47/50* | (2017.01) | |
| *A61K 47/65* | (2017.01) | |
| *A61K 31/4745* | (2006.01) | |

(52) U.S. Cl.
CPC .............. *A61K 9/19* (2013.01); *A61K 9/0019* (2013.01); *A61K 9/08* (2013.01); *A61K 9/1611* (2013.01); *A61K 9/1617* (2013.01); *A61K 9/1623* (2013.01); *A61K 9/1682* (2013.01); *A61K 31/4745* (2013.01); *A61K 47/50* (2017.08); *A61K 47/60* (2017.08); *A61K 47/65* (2017.08)

(58) Field of Classification Search
CPC ... A61K 9/19; A61K 9/08; A61K 9/00; A61K 9/16; A61K 47/60; A61K 47/50; A61K 47/65
See application file for complete search history.

(56) References Cited

U.S. PATENT DOCUMENTS 9,700,633 B2 *  7/2017  Wang ............... A61K 47/48246

OTHER PUBLICATIONS

Paranjpe et al., Anti-Cancer Drugs, 2005, vol. 16 No. 7, 763-775.*

* cited by examiner

*Primary Examiner* — Sun Jae Yoo
(74) *Attorney, Agent, or Firm* — Flener IP & Business Law; Zareefa B. Flener

(57) ABSTRACT

A pharmaceutical composition of a polyethylene glycol-modified camptothecin derivative and a preparation method thereof. The pharmaceutical composition is prepared mainly from following components: a camptothecin derivative modified by polyethylene glycol, a pH value adjustment agent and water for injection. The pharmaceutical composition has high stability.

11 Claims, No Drawings

PHARMACEUTICAL COMPOSITION OF POLYETHYLENE GLYCOL-MODIFIED CAMPTOTHECIN DERIVATIVE AND PREPARATION METHOD THEREOF

CROSS-REFERENCE TO RELATED APPLICATION

This application is a continuation application of International patent application No. PCT/CN2015/096151, filed on Dec. 1, 2015, which claims the benefit and priority of Chinese patent application No. CN201410739978.X, filed on Dec. 5, 2014, each of which is incorporated herein by reference in its entirety and for all purposes.

FIELD OF THE INVENTION

The present invention belongs to the field of medicine, and in particular to a pharmaceutical composition of a polyethylene glycol-modified camptothecin derivative for injection and a preparation method and an application thereof.

BACKGROUND OF THE INVENTION

Camptothecin (CPT, Formula 1) is a natural product isolated from Nyssaceae plant *Camptotheca acuminata*, which was introduced into clinical practice in the early 1970s due to its excellent anticancer activity, later, due to diarrhea, hemorrhagic cystitis and other serious side effects, the clinical trials were terminated.

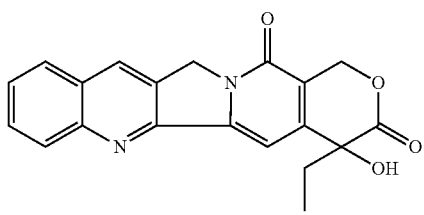

1

Since the 1990s, a number of camptothecin derivatives have come into the market or entered into clinical studies successively, including 10-hydroxycamptothecin, 7-ethyl-10-hydroxycamptothecin, 9-nitrocamptothecin, 9-aminocamptothecin, irinotecan (CPT-11, Formula 2), topotecan and belotecan, exatecan, lurtotecan, diflomotecan, gimatecan, karenitecin, and so on. Among them, irinotecan has a very broad antitumor spectrum, and Phase I, II clinical study results show that the drug has a positive effect on chemotherapy-resistant tumors such as metastatic colorectal cancer, non-small cell lung cancer, ovarian cancer and cervical cancer, and also has a certain effect on gastric cancer, malignant lymphoma non-Hodgkin's lymphoma, breast cancer, small cell lung cancer, skin cancer, pancreatic cancer. It is now mainly used as an effective drug for the treatment of advanced colorectal cancer, and can still be effective for 5-FU resistant cases.

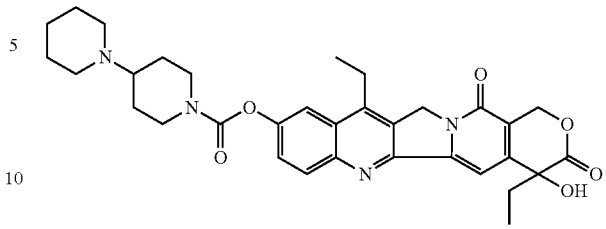

2

However, camptothecin derivatives, including irinotecan, have a good anticancer activity, but still have some shortcomings, such as a poor solubility in water, great toxic side effects. The common adverse reactions are anorexia, nausea, vomit, diarrhea, leukopenia and neutropenia, anemia and thrombocytopenia, alopecia and acetylcholine syndrome. Especially diarrhea is the most common, nearly 90% of the subjects have diarrhea, of which nearly 30% have severe diarrhea.

Polyethylene glycol modification technology is a new technology developed rapidly in recent years, which is linking polyethylene glycol after activation to a drug molecule or surface to form a prodrug, and when the polyethylene glycol-drug complex enters the body, it can slowly release the drug molecule thus to produce curative effect. The polyethylene glycol-modified drug molecules have the following advantages: 1, increased water solubility of drugs; 2, reduced toxicity; 3, extended cycle half-life of drugs, reduced medication times, improved patient compliance, improved quality of life, reduced treatment cost; 4, reduced enzyme degradation effect, improved bioavailability.

Polyethylene glycol modification technology has been applied in camptothecin derivatives, WO2005028539 reports a series of compounds in which a multi-branched polyethylene glycol is linked to irinotecan, currently, in which one drug named etirinotecan pegol (Formula 3) is undergoing Phase III clinical trials for the treatment of metastatic breast cancer and colorectal cancer in a number of countries.

WO2007081596 reports a series of compounds in which a polyethylene glycol is linked to 7-ethyl-10-hydroxycamptothecin (an active metabolite of irinotecan in vivo), currently, in which one drug named firtecan pegol is undergoing Phase II clinical trials for the treatment of breast cancer and colorectal cancer in a number of countries.

CN103083680 discloses a polyethylene glycol-amino acid oligopeptide-irinotecan conjugate as shown in formula (4) having antitumor activity for the treatment of colorectal cancer, ovarian cancer and lung cancer, etc.

There have been no reports of pharmaceutical compositions of polyethylene glycol-modified camptothecin derivatives for injection in the prior art.

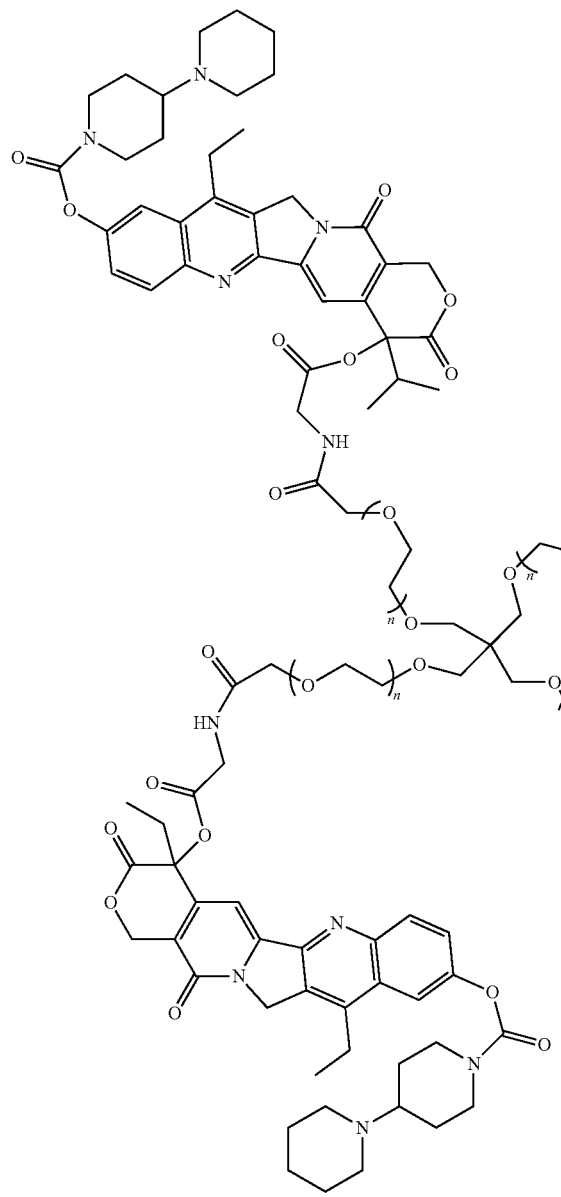
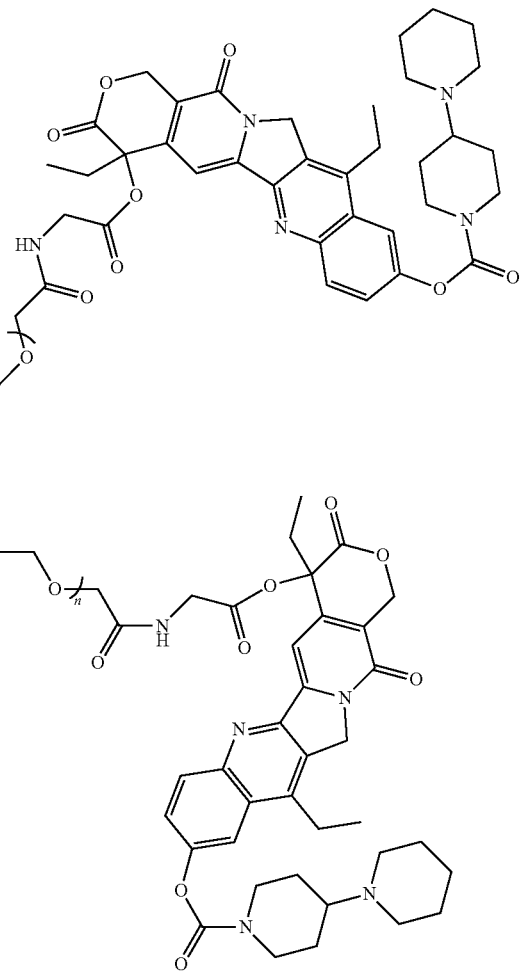

In the prior art, the pharmaceutical composition of the camptothecin derivative is mostly a lyophilized preparation for injection, and CN103655491 reports a pharmaceutical composition of an irinotecan hydrochloride and a preparation method thereof, wherein the irinotecan hydrochloride is prepared into a lyophilized preparation, however, in the preparation process not only irinotecan hydrochloride and water for injection are used, lactose, ethanol and other additives are also used, which may not only increase the cost of product, more importantly, introduce substances that may affect the efficacy and produce side effects, resulting in uncertainty factors for the drug safety.

In addition, in the prior art, high molecular weight polyethylene glycol amino acid oligopeptides are linked to camptothecin derivative through ester bonds, the ester bonds have a poor stability, especially in a humid environment is easier to be hydrolyzed slowly and thus release the camptothecin derivative, which thereby affects the effect of polyethylene glycol modified drugs, and in the preparation, storage and use of injections, particularly lyophilized preparations for injection, contact with the humid environment is unavoidable, resulting in a slow degradation of the pharmaceutical composition of the polyethylene glycol-modified camptothecin derivative, which affects the drug stability.

SUMMARY OF THE INVENTION

It is one object of the present invention to provide a pharmaceutical composition of a polyethylene glycol-modified camptothecin derivative which has a high stability and can conform to the molding requirements and quality requirements of preparation and a preparation method thereof.

It is another object of the present invention to solve the problem that the polyethylene glycol-modified camptothecin derivative has a poor stability, and is easier to be slowly hydrolyzed in a humid environment and thus release the camptothecin derivative, which may thereby affect the effect of the polyethylene glycol-modified drug.

It is also one object of the present invention to provide an application of the pharmaceutical composition of polyethylene glycol-modified camptothecin derivative in the treatment of cancer.

Thus, one aspect of the present invention is to provide a pharmaceutical composition of a polyethylene glycol-modified camptothecin derivative which is mainly prepared by the following components: a polyethylene glycol-modified camptothecin derivative, pH adjuster and water for injection, wherein the pharmaceutical composition comprises 100 to 500 mg of the polyethylene glycol-modified camptothecin derivative.

The polyethylene glycol-modified camptothecin derivative of the present invention has the structure of the general formula (I):

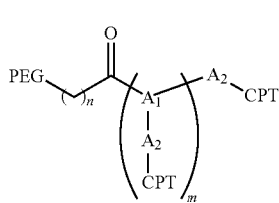

wherein:

PEG represents a polyethylene glycol residue, PEG has a molecular weight of 300 to 60,000 Daltons;

$A_1$ and $A_2$ represent the same or different amino acid residues;

m is an integer of 2 to 12, preferably, in is 2 to 6, more preferably, in is 2 or 3;

n is an integer of 0 to 6, preferably, n is 0 to 3, more preferably, n is 0, 1, 2 or 3;

and CPT is a camptothecin derivative residue, and the camptothecin derivative is selected from the group consisting of: 10-hydroxycamptothecin, 7-ethyl-10-hydroxycamptothecin, 9-nitrocamptothecin, 9-aminocamptothecin, irinotecan, topotecan and belotecan, exatecan, lurtotecan, diflutamide, diflomotecan, gimatecan or karenitecin. Preferably, the camptothecin derivative is 7-ethyl-10-hydroxycamptothecin (Formula 5) or irinotecan (Formula 2).

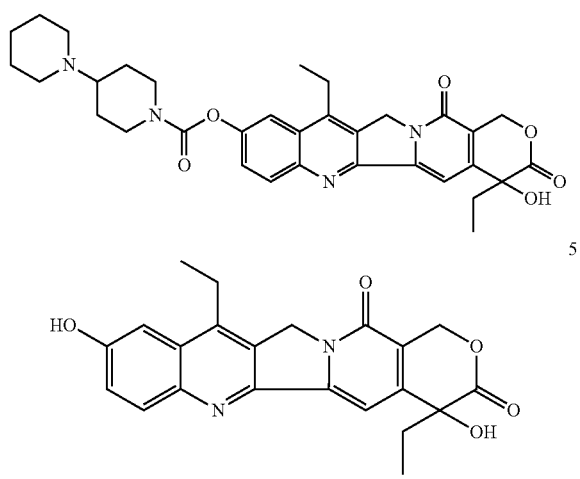

Preferably, the PEG of the present invention has a molecular weight of 20,000 to 40,000 Daltons.

The PEG of the present invention may be a straight-chain, Y-type or multi-branched polyethylene glycol residue.

When PEG is a straight-chain polyethylene glycol residue, it has the structure of general formula (II):

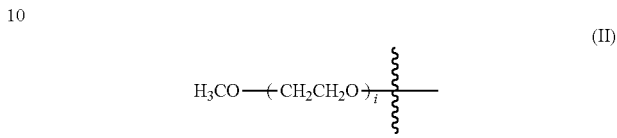

When PEG is a Y-type polyethylene glycol residue, it has the structure of general formula (III):

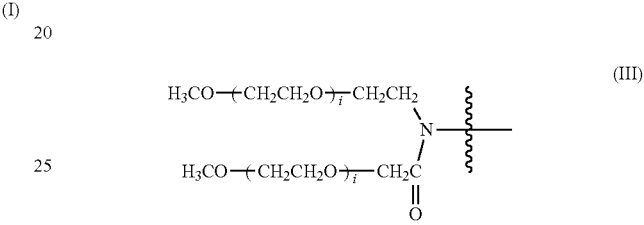

wherein i is an integer of 10 to 1,500, preferably, i is an integer of 400 to 500.

When PEG is a multi-branched polyethylene glycol residue, it has the structure of general formula (IV):

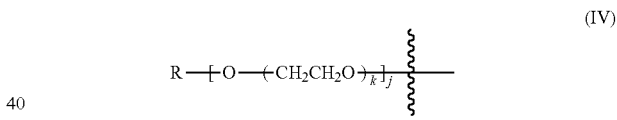

wherein:

k is an integer of 10 to 1,500, preferably, k is an integer of 160 to 180;

j is an integer of 3 to 8, preferably, j is 4;

and R is a core molecule of the multi-branched polyethylene glycol, and R is selected from the group consisting of residues of pentaerythritol, methylglucoside, sucrose, diethylene glycol, propylene glycol, glycerol or polyglycerol.

$A_1$ and $A_2$ in the present invention represent the same or different amino acid residues, and $A_1$ and $A_2$ are independently selected from the group consisting of aspartic acid, glutamic acid, glycine, alanine, leucine, isoleucine, valine, phenylalanine or methionine. Preferably, the $A_1$ of the present invention is selected from aspartic acid or glutamic acid, the $A_2$ is selected from the group consisting of glycine, alanine, leucine, isoleucine, valine, phenylalanine or methionine. More preferably, $A_1$ is glutamic acid, $A_2$ is glycine.

In a specific embodiment of the present invention, when in is preferably 2, n is preferably 1 in the structure of the general formula (I), the polyethylene glycol-modified camptothecin derivative has the structure of general formula (V):

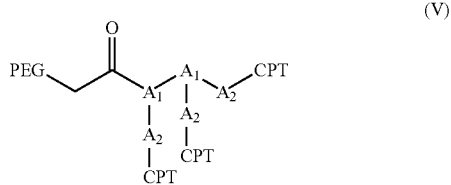
(V)

In a specific embodiment of the present invention, when in is preferably 3, n is preferably 1 in the structure of the general formula (I), the polyethylene glycol-modified camptothecin derivative has the structure of general formula (VI):

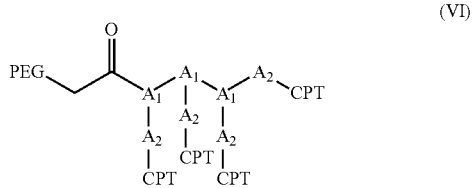
(VI)

In a more preferred embodiment of the present invention, the polyethylene glycol-modified camptothecin derivative having the structure of general formula (I) is:

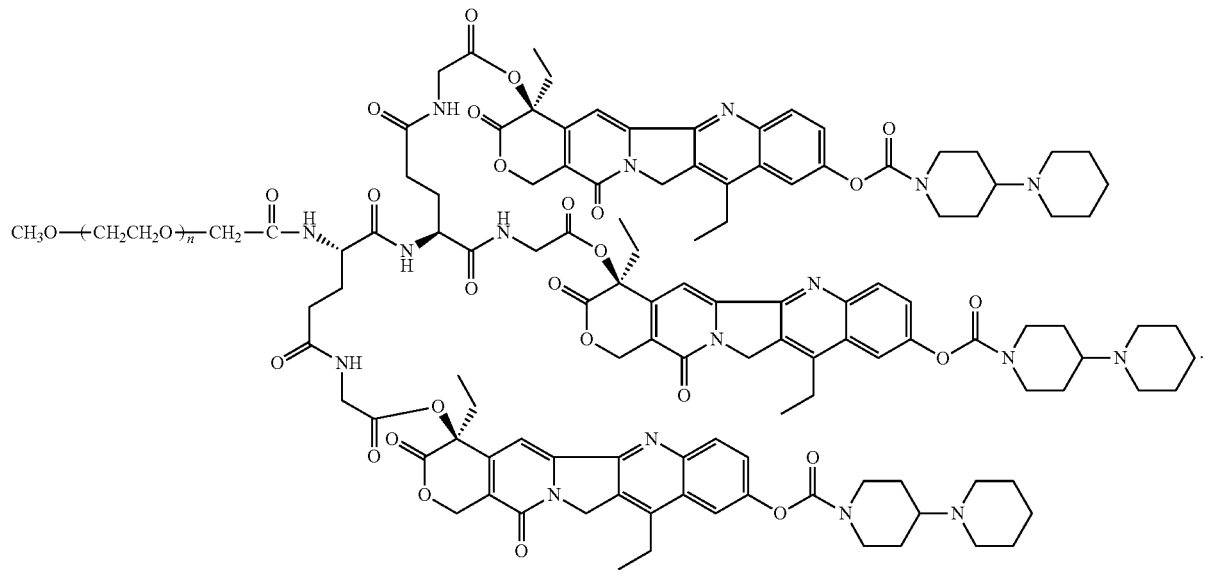

The content of the polyethylene glycol-modified camptothecin derivative in the pharmaceutical composition of the present invention can be determined according to the therapeutic dosage of the polyethylene glycol-modified camptothecin derivative in the art. The polyethylene glycol-modified camptothecin derivatives having different structures may be added to the pharmaceutical compositions in varying amounts. In a preferred embodiment of the present invention, the pharmaceutical composition comprises 100 to 500 mg of polyethylene glycol-modified camptothecin derivative, preferably 200 to 500 mg.

The pH adjuster of the present invention is one or a combination of more than two selected from the group consisting of hydrochloric acid, hydrobromic acid, sulfuric acid, nitric acid, phosphoric acid, carbonic acid, toluenesulfonic acid, methanesulfonic acid, acetic acid, citric acid, malonic acid, tartaric acid, succinic acid, benzoic acid, ascorbic acid, α-ketoglutaric acid or α-glycerophosphoric acid. Preferably, the pH adjuster is one or a combination more than two selected from the group consisting of hydrochloric acid, acetic acid and phosphoric acid. More preferably, the pH adjuster is hydrochloric acid. The pH adjuster in the present invention is used to adjust the pH of the aqueous solution for injection comprising the polyethylene glycol-modified camptothecin derivative to 3.0 to 4.0. Since the polyethylene glycol-modified camptothecin derivatives are more stable in an acidic environment, especially acidic environment with a pH value lower than 4.0, and a faintly acidic environment with a pH value higher than 4.0, neutral or alkaline environments can cause a rapid degradation of polyethylene glycol-modified camptothecin derivatives. In the preparation process of the pharmaceutical composition of the polyethylene glycol-modified camptothecin derivative, the pH value of aqueous solution for injection comprising the polyethylene glycol-modified camptothecin derivative is adjusted to lower than 4.0 by the pH adjuster, and then a lyophilized preparation is prepared in accordance with a freeze-drying procedure. When the pH is lower than 3.0, both the appearance color of the lyophilized preparation product and the color after re-dissolution are darker, suggesting that the preparation product contains more colored impurities, so the pH is preferably in the range of 3.0 to 4.0. More preferably, the pH adjuster is used to adjust the pH of the aqueous solution for injection containing the polyethylene glycol-modified camptothecin derivative to 3.4 to 3.6.

In the present invention, the water for injection is used to provide an adjuvant material used for preparing the polyethylene glycol-modified camptothecin derivative into a preparation for injection. The water for injection is used to dissolve and dilute the polyethylene glycol-modified camptothecin derivative, which may be added in accordance with conventional additions in the art. In a specific embodiment of the present invention, the ratio of the amount of the water for injection and that of the polyethylene glycol-modified camptothecin derivative may be 10 to 80 ml/1 mg, preferably 20 to 60 ml/1 mg.

In a specific embodiment of the present invention, in addition to the polyethylene glycol-modified camptothecin derivative, the pH adjuster and the water for injection, the component further comprises a lyophilized excipient. The amount of the lyophilized excipient may be 0 to 10% (W/V), more preferably 0 to 5% (W/V) of the aqueous solution for injection comprising the polyethylene glycol-modified camptothecin derivative. The lyophilized excipient is one or more than two of mannitol, lactose, glucose, hydrolyzed gel, glycine or dextran. Preferably, the lyophilized excipient is mannitol and/or lactose. More preferably, the lyophilized excipient is mannitol.

The pharmaceutical composition of the polyethylene glycol-modified camptothecin derivative of the present invention is a solution injection, a suspension injection, an emulsion injection or sterile powder for injection. Preferably, the pharmaceutical composition is sterile powder for injection; more preferably, the pharmaceutical composition is a lyophilized preparation for injection.

Another aspect of the present invention is to provide a preparation method of the pharmaceutical composition of the polyethylene glycol-modified camptothecin derivative, the method comprises the following steps: (1) taking the polyethylene glycol-modified camptothecin derivative and lyophilized excipient, adding water for injection with a total volume of water for injection in the composition of 70% to 90%, stirring to make the solution completely dissolved; (2) adjusting the pH to 3.0 to 4.0 with the pH adjuster, adding water for injection to a full dose; (3) freeze-drying to obtain the product.

In a preferred embodiment of the present invention, the total volume of the water for injection added into components in the step (1) is 90%; stirring in the step (1) is stirring to make the solution completely dissolved, and the pH is adjusted to 3.0 to 4.0 with the pH adjuster in the step (2), the temperature in the process of adding water for injection to the full dose is lower than 30° C., preferably 15 to 30° C.; the preparation of the pharmaceutical composition of the polyethylene glycol-modified camptothecin derivative is completed within 10 hours, preferably within 8 hours.

In a specific embodiment of the present invention, the freeze-drying step in the step (3) is preferably pre-freezing at −20° C. to −40° C. for 4 to 8 hours and then completing sublimation drying within 40 to 60 hours, finally desorption drying at 25° C. for 4 to 8 hours. Preferably, the pre-freezing temperature is −40° C.

Yet another aspect of the present invention is to provide an application of the polyethylene glycol-modified camptothecin derivative pharmaceutical composition in the treatment of cancer. Preferably, the cancer is one of colorectal cancer, ovarian cancer, and lung cancer.

The pharmaceutical composition of the polyethylene glycol-modified camptothecin derivative of the present invention has a high stability and can conform to the molding requirements and quality requirements of preparation, and the stability of the preparation can be effectively improved by adjusting the pH of the medicated solution in the preparation method. But also by industrialized production, the pharmaceutical composition has been proved to may have very good process stability through an impact factor test, compatibility stability test, acceleration test, long-term test.

DETAILED DESCRIPTION OF THE INVENTION

The present invention will be further described in detail with reference to the following examples.

In the present invention, the straight-chain polyethylene glycol (with a molecular weight of 20,000 Daltons)-glutamate glycine pentapeptide-irinotecan is prepared according to patent CN103083680A, and other reagents are commercially available.

EXAMPLE 1

Lyophilized Preparation of Straight-chain Polyethylene Glycol (with a Molecular Weight of 20,000 Daltons)-glutamate Glycine Pentapeptide-irinotecan and Preparation thereof (Prescription 1)

Each 15 ampoules of the lyophilized preparation has a composition of:

| | |
|---|---|
| Straight-chain polyethylene glycol-glutamate glycine pentapeptide-irinotecan | 4.275 g |
| Hydrochloric acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 2.0 with 1.0% hydrochloric acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 2

Lyophilized Preparation of Straight-chain Polyethylene Glycol (with a Molecular Weight of 20,000 Daltons)-glutamate Glycine Pentapeptide-irinotecan and Preparation thereof (Prescription 2)

Each 15 ampoules of the lyophilized preparation has a prescription composition of:

| | |
|---|---|
| Straight-chain polyethylene glycol-glutamate glycine pentapeptide-irinotecan | 4.275 g |
| Hydrochloric acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 3.0 with 1.0% hydrochloric acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 3

Lyophilized Preparation of Straight-chain Polyethylene Glycol (with a Molecular Weight of 20,000 Daltons)-glutamate Glycine Pentapeptide-irinotecan and Preparation thereof (Prescription 3)

Each 15 ampoules of the lyophilized preparation has a prescription composition of:

| | |
|---|---|
| Straight-chain polyethylene glycol-glutamate glycine pentapeptide-irinotecan | 4.275 g |
| Hydrochloric acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 4.0 with 1.0% hydrochloric acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 4

Lyophilized Preparation of Straight-chain Polyethylene Glycol (with a Molecular Weight of 20,000 Daltons)-glutamate Glycine Pentapeptide-irinotecan and Preparation thereof (Prescription 4)

Each 15 ampoules of the lyophilized preparation has a prescription composition of:

| | |
|---|---|
| Straight-chain polyethylene glycol-glutamate glycine pentapeptide-irinotecan | 4.275 g |
| Hydrochloric acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 5.0 with 1.0% hydrochloric acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 5

Investigation of the pH Value Range of the Prepared Solution

The stability of the samples with the prepared solution pH value of 2, 3, 4 and 5, respectively, were investigated by taking the appearance character, related substances and solution clarity as the main indexes.

The prepared samples of different prescriptions were placed under the condition of high temperature (40° C.), respectively, and sampled at $5^{th}$, $10^{th}$ day, the appearance character, clarity and small molecules related substances of the samples were investigated, and the results are shown in Table 1.

TABLE 1

Investigation results of the prescriptions with different pH values

| Prescription number | Time (day) | Appearance character | Color and clarity after re-dissolution | Irinotecan (ppm) | Maximum individual impurity (ppm) | Total impurity (ppm) |
|---|---|---|---|---|---|---|
| Prescription 1 | Day 0 | Yellow green block | Transparent yellow green | 4.06 | 76.10 | 114.2 |
| | Day 5 | Yellow green block | Transparent yellow green | 2.23 | 100.4 | 166.6 |
| | Day 10 | Yellow green block | Transparent yellow green | 30.28 | 189.3 | 276.2 |
| Prescription 2 | Day 0 | Light yellow block | Transparent light yellow | 6.09 | 78.97 | 118.3 |
| | Day 5 | Light yellow block | Transparent light yellow | 23.57 | 94.53 | 158.0 |
| | Day 10 | Light yellow block | Transparent light yellow | 36.82 | 174.2 | 259.2 |
| Prescription 3 | Day 0 | Light yellow block | Transparent light yellow | 12.79 | 84.17 | 130.7 |
| | Day 5 | Light yellow block | Transparent light yellow | 30.73 | 95.45 | 168.8 |
| | Day 10 | Light yellow block | Transparent light yellow | 45.10 | 174.4 | 268.0 |
| Prescription 4 | Day 0 | Light yellow block | Transparent light yellow | 26.16 | 83.80 | 144.2 |
| | Day 5 | Light yellow block | Transparent light yellow | 70.17 | 131.8 | 248.7 |
| | Day 10 | Light yellow block | Transparent light yellow | 85.69 | 223.2 | 366.2 |

It can be seen from the above results that, when the pH value of the prepared solution is low, the samples are yellow green, and when the pH value of the prepared solution is greater than 3, the samples are light yellow. The samples with Prescription 1, 2, 3 have a relatively small change of small molecular impurities, and a relatively good prescription stability after being placed at a high temperature of 40° C. for 10 days, however, the color of the sample with the prescription 1 is yellow green, which is greatly different from the character of the samples with other prescriptions. Therefore, under the condition of a pH value range of 3.0 to 4.0, the stability of the prescription can be relatively good.

EXAMPLE 6

Lyophilized Preparation of Straight-chain Polyethylene Glycol (with a Molecular Weight of 20,000 Daltons)-glutamate Glycine Pentapeptide-irinotecan and Preparation thereof (Prescription 5)

Each 15 ampoules of the lyophilized preparation has a prescription composition of:

| | |
|---|---|
| Straight-chain polyethylene glycol-glutamate glycine pentapeptide-irinotecan | 4.275 g |
| Hydrochloric acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 3.4 to 3.6 with 1.0% hydrochloric acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 7

Detailed Investigation of the pH Value Range of the Prepared Solution

The pH value was investigated more detailed in the range of pH 3.0 to 4.0, the stability of the samples with the prepared solution pH value of 3.0, 3.4 to 3.6, 4.0, respectively, were investigated by taking the appearance character, related substances and solution clarity as the main indexes.

The prepared samples of different prescriptions were placed under the condition of high temperature (40° C.), respectively, and sampled at 5$^{th}$, 10$^{th}$ day, the appearance character, clarity and small molecules related substances of the samples were investigated, and the results are shown in Table 2.

TABLE 2

Investigation results of the prescriptions with detailed pH values

| Prescription number | Time (day) | Appearance character | Color and clarity after re-dissolution | Innotecan (ppm) | Maximum individual impurity (ppm) | Total impurity (ppm) |
|---|---|---|---|---|---|---|
| Prescription 2 | Day 0 | Light yellow block | Transparent light yellow | 6.27 | 15.81 | 49.64 |
| | Day 5 | Light yellow block | Transparent light yellow | 18.74 | 119.6 | 191.6 |
| | Day 10 | Light yellow block | Transparent light yellow | 33.01 | 117.7 | 192.5 |
| Prescription 5 | Day 0 | Light yellow block | Transparent light yellow | 8.24 | 16.00 | 53.30 |
| | Day 5 | Light yellow block | Transparent light yellow | 19.55 | 122.4 | 190.0 |
| | Day 10 | Light yellow block | Transparent light yellow | 33.64 | 113.3 | 186.8 |
| Prescription 3 | Day 0 | Light yellow block | Transparent light yellow | 15.87 | 19.58 | 68.09 |
| | Day 5 | Light yellow block | Transparent light yellow | 29.46 | 88.36 | 203.2 |
| | Day 10 | Light yellow block | Transparent light yellow | 54.20 | 100.3 | 211.6 |

It can be seen from the above results that, in the range of prepared solution pH value of 3.0 to 4.0, the samples have a good stability, and have a relatively small change of small molecular impurities after being placed at a high temperature of 40° C. for 10 days, a pH range of the prepared solution in the product according to the present invention of 3.0 to 4.0, and an internal control pH of 3.4 to 3.6 are determined.

EXAMPLE 8

Lyophilized Preparation of Straight-chain Polyethylene Glycol (with a Molecular Weight of 20,000 Daltons)-glutamate Glycine Pentapeptide-irinotecan and Preparation thereof (Prescription 6)

Each 15 ampoules of the lyophilized preparation has a prescription composition of:

| | |
|---|---|
| Straight-chain polyethylene glycol-glutamate glycine pentapeptide-irinotecan | 4.275 g |
| Acetic acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 3.4 to 3.6 with acetic acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 9

Lyophilized Preparation of Straight-chain Polyethylene Glycol (with a Molecular Weight of 20,000 Daltons)-glutamate Glycine Pentapeptide-irinotecan and Preparation thereof (Prescription 7)

Each 15 ampoules of the lyophilized preparation has a prescription composition of:

| | |
|---|---|
| Straight-chain polyethylene glycol-glutamate glycine pentapeptide-irinotecan | 4.275 g |
| Citric acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 3.4 to 3.6 with citric acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 10

Lyophilized Preparation of Straight-chain Polyethylene Glycol (with a Molecular Weight of 20,000 Daltons)-glutamate Glycine Pentapeptide-irinotecan and Preparation thereof (Prescription 8)

Each 15 ampoules of the lyophilized preparation has a prescription composition of:

| | |
|---|---|
| Straight-chain polyethylene glycol-glutamate glycine pentapeptide-irinotecan | 4.275 g |
| Phosphoric acid | Appropriate amount |
| Water for injection | Added to 90 mL |

Preparation process: a prescription amount of the straight-chain polyethylene glycol-glutamate glycine pentapeptide-irinotecan was taken, and was added with 80 mL of water for injection, and stirred for 0.5 hour to make the solution completely dissolved, and the pH was adjusted to 3.4 to 3.6 with phosphoric acid, and water for injection was added to the full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 11

Investigation of the pH Adjuster

The stability of the samples with different pH adjusters were investigated by taking the appearance character, related substances and solution clarity as the main indexes, and using hydrochloric acid, acetic acid, citric acid and phosphoric acid as pH adjuster, respectively, to adjust the prepared solution pH value to 3.4 to 3.6.

The samples were placed under the condition of a high temperature (40° C.), respectively, and sampled at $5^{th}$, $10^{th}$ day, the appearance character, clarity and small molecules related substances of the samples were investigated, and the results are shown in Table 3.

TABLE 3

Investigation results of the prescriptions with different pH adjusters

| Prescription number | Time (day) | Appearance character | Color and clarity after re-dissolution | Irinotecan (ppm) | Maximum individual impurity (ppm) | Total impurity (ppm) |
|---|---|---|---|---|---|---|
| Prescription 5 | Day 0 | Light yellow block | Transparent light yellow | 17.53 | 24.29 | 75.03 |
| | Day 5 | Light yellow block | Transparent light yellow | 16.87 | 24.74 | 83.25 |
| | Day 10 | Light yellow block | Transparent light yellow | 29.67 | 46.12 | 125.0 |
| Prescription 6 | Day 0 | Light yellow block | Transparent light yellow | 21.20 | 28.69 | 75.74 |
| | Day 5 | Light yellow block | Transparent light yellow | 32.26 | 38.40 | 135.1 |
| | Day 10 | Light yellow block | Transparent light yellow | 32.64 | 50.51 | 137.0 |
| Prescription 7 | Day 0 | Light yellow block | Transparent light yellow | 146.6 | 60.99 | 281.8 |
| | Day 5 | Light yellow block | Transparent light yellow | 162.0 | 62.96 | 324.2 |
| | Day 10 | Light yellow block | Transparent light yellow | 176.1 | 63.01 | 364.2 |
| Prescription 8 | Day 0 | Light yellow block | Transparent light yellow | 32.95 | 25.23 | 81.61 |
| | Day 5 | Light yellow block | Transparent light yellow | 47.00 | 46.18 | 146.4 |
| | Day 10 | Light yellow block | Transparent light yellow | 59.19 | 67.02 | 180.8 |

In the prescription samples with different pH adjusters, the sample with citric acid as the pH adjuster has a poor stability, and the other prescriptions are not very different, however, the sample with hydrochloric acid as the pH adjuster has the best stability relatively.

EXAMPLE 12

Lyophilized Preparation of Straight-chain Polyethylene Glycol (with a Molecular Weight of 20,000 Daltons)-glutamate Glycine Pentapeptide-irinotecan and Preparation thereof (Prescription 9)

Each 10 ampoules of the lyophilized preparation has a prescription composition of:

| | |
|---|---|
| Straight-chain polyethylene glycol-glutamate glycine pentapeptide-irinotecan | 2.85 g |

-continued

| | |
|---|---|
| mannitol | 1.8 g (3%) |
| Hydrochloric acid | Appropriate amount |
| Water for injection | Added to 60 mL |

Preparation process: a prescription amount of the straight-chain polyethylene glycol-glutamate glycine pentapeptide-irinotecan and mannitol were taken, and was added with 54 mL of water for injection, and stirred for 0.5 hour to make the solution completely dissolved, and the pH was adjusted to 3.4 to 3.6 with 1.0% hydrochloric acid, and water for injection was added to the full dose. The solution obtained was filtered through a 0.22 µm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 13

Lyophilized Preparation of Straight-chain Polyethylene Glycol (with a Molecular Weight of 20,000 Daltons)-glutamate Glycine Pentapeptide-irinotecan and Preparation thereof (Prescription 10)

Each 10 ampoules of the lyophilized preparation has a prescription composition of:

| | |
|---|---|
| Straight-chain polyethylene glycol-glutamate glycine pentapeptide-irinotecan | 2.85 g |
| mannitol | 3.0 g (5%) |
| Hydrochloric acid | Appropriate amount |
| Water for injection | Added to 60 mL |

Preparation process: a prescription amount of the straight-chain polyethylene glycol-glutamate glycine pentapeptide-irinotecan and mannitol were taken, and was added with 54 mL of water for injection, and stirred for 0.5 hour to make the solution completely dissolved, and the pH was adjusted to 3.4 to 3.6 with 1.0% hydrochloric acid, and water for injection was added to the full dose. The solution obtained was filtered through a 0.22 µm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 14

Effect of Lyophilized Excipient on Formability of Lyophilized Samples

The effect of dosage of lyophilized excipient mannitol of 0%, 3%, 5%, respectively, on formability of the preparation was investigated by taking lyophilized formability, re-dissolvability as the main indicators, to optimize different prescription samples, and the results are shown in Table 4.

TABLE 4

Investigation results of the prescriptions with different dosage of mannitol

| Prescription number | Ratio of mannitol | Lyophilized formability | Re-dissolvability |
|---|---|---|---|
| Prescription 5 | 0% | The content was loose block with a fine and smooth appearance, no cracks, good skeleton, without shrinking or collapse. | The preparation was dissolved when water was added, the solution had a good clarity. |
| Prescription 9 | 3% | | |
| Prescription 10 | 5% | | |

It can be seen from the above results that, the addition of mannitol has no effect on the formability and re-dissolvability of the product. Without the addition of mannitol, the lyophilized formability is good, and the content is loose block with a fine and smooth appearance, no cracks, good skeleton, without shrinking or collapse; and the re-dissolvability is good, the preparation is dissolved when water is added, and the solution has a good clarity.

As the product itself has a good lyophilized formability, it can be formed well without addition of any lyophilized excipients, and can conform to the quality requirements of lyophilized preparations.

EXAMPLE 15

Investigation of Stability of the Prepared Solution

The preparation temperature and the preparation time of solution in the solution preparation process were mainly investigated in this experiment. The stability of the solution under the condition of preparation temperature of 30° C., 50° C. and 70° C., and preparation time of 0, 2, 4 and 8 hours were investigated by taking the related substances as the main index.

3.8 g of the straight-chain polyethylene glycol-glutamate glycine pentapeptide-irinotecan (3 copies were prepared in parallel) were weighed, respectively, and was added with 72 mL of water for injection, and stirred to make the solution completely dissolved, and the pH was adjusted to 3.4 to 3.6 with 1.0% hydrochloric acid, and added to a constant volume which was the full dose (80 ml).

The solution was placed at constant temperature of 30° C. (Process 1), 50° C. (Process 2) and 70° C. (Process 3) (with shaking from time to time), respectively, and sampled at $0^{th}$, $2^{nd}$, $4^{th}$, $8^{th}$ hour. The results are shown in Table 5.

TABLE 5

Investigation results of stability of the prepared solution (small molecule related substances)

| Process number | Solution preparation temperature | Solution color and clarity | Solution placement time (hours) | Irinotecan (ppm) | Maximum individual impurity (ppm) | Total impurity (ppm) |
|---|---|---|---|---|---|---|
| Process 1 | 30° C. | Light yellow transparent solution | 0 | 8.12 | 18.33 | 56.74 |
| | | | 2 | 9.39 | 19.97 | 62.12 |
| | | | 4 | 10.22 | 20.89 | 61.99 |
| | | | 8 | 17.58 | 25.77 | 84.42 |
| Process | 50° C. | Light yellow | 0 | 4.53 | 17.69 | 45.48 |
| | | | 2 | 52.74 | 52.78 | 182.7 |

TABLE 5-continued

Investigation results of stability of the prepared solution (small molecule related substances)

| Process number | Solution preparation temperature | Solution color and clarity | Solution placement time (hours) | Irinotecan (ppm) | Maximum individual impurity (ppm) | Total impurity (ppm) |
|---|---|---|---|---|---|---|
| 2 | | transparent solution | 4 | 41.04 | 47.14 | 149.9 |
| | | | 8 | 75.99 | 71.76 | 258.9 |
| Process 3 | 70° C. | Light yellow transparent solution | 0 | 3.20 | 15.91 | 41.76 |
| | | | 2 | 75.12 | 59.15 | 233.6 |
| | | | 4 | 138.85 | 112.3 | 399.1 |
| | | | 8 | 268.03 | 173.9 | 703.0 |

It can be seen from the above results, with the solution preparation temperature raises, solution preparation time increases, the solution impurities are gradually increased. When Process 2 and Process 3 with solution preparation temperature of 50° C., 70° C., respectively are adopted, the small molecule impurities are significantly increased, therefore in the solution preparation process, the solution preparation temperature should be controlled not higher than 30° C., while the solution preparation, filtration, filling time should not exceed 8 hours.

EXAMPLE 16

Lyophilized Preparation of Y-type Polyethylene Glycol (with a Molecular Weight of 40,000 Daltons)-glutamate Glycine Pentapeptide-irinotecan and Preparation thereof Each 15 ampoules of the lyophilized preparation has a prescription composition of:

| Y-type polyethylene glycol-glutamate glycine pentapeptide-irinotecan | 7.395 g |
|---|---|
| Hydrochloric acid | Appropriate amount |
| Water for injection | Added to 90 mL |

Preparation process: a prescription amount of the Y-type polyethylene glycol-glutamate glycine pentapeptide-irinotecan was taken, and was added with 80 mL of water for injection, and stirred for 0.5 hour to make the solution completely dissolved, and the pH was adjusted to 3.4 to 3.6 with 1.0% hydrochloric acid, and water for injection was added to full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 17

Lyophilized Preparation of Four-branched Polyethylene Glycol (with a Molecular Weight of 40,000 Daltons)-glutamate Glycine Icosapeptide-irinotecan and Preparation thereof Each 15 ampoules of the lyophilized preparation has a prescription composition of:

| Four-branched polyethylene glycol-glutamate glycine icosapeptide-irinotecan | 2.355 g |
|---|---|
| Hydrochloric acid | Appropriate amount |
| Water for injection | Added to 90 mL |

Preparation process: a prescription amount of the four-branched polyethylene glycol-glutamate glycine icosapeptide-irinotecan was taken, and was added with 80 mL of water for injection, and stirred for 0.5 hour to make the solution completely dissolved, and the pH was adjusted to 3.4 to 3.6 with 1.0% hydrochloric acid, and water for injection was added to full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 18

Lyophilized Preparation of Straight-chain Polyethylene Glycol (with a Molecular Weight of 20,000 Daltons)-glutamate Glycine Pentapeptide-7-ethyl-10-hydroxycamptothecin and Preparation thereof Each 15 ampoules of the lyophilized preparation has a prescription composition of:

| Straight-chain polyethylene glycol-glutamate glycine pentapeptide-7-ethyl-10-hydroxycamptothecin | 4.155 g |
|---|---|
| Hydrochloric acid | Appropriate amount |
| Water for injection | Added to 90 mL |

Preparation process: a prescription amount of the straight-chain polyethylene glycol-glutamate glycine pentapeptide-7-ethyl-10-hydroxycamptothecin was taken, and was added with 80 mL of water for injection, and stirred for 0.5 hour to make the solution completely dissolved, and the pH was adjusted to 3.4 to 3.6 with 1.0% hydrochloric acid, and water for injection was added to full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 19

Lyophilized Preparation of Y-type Polyethylene Glycol (with a Molecular Weight of 40,000 Daltons)-glutamate Glycine Pentapeptide-7-ethyl-10-hydroxycamptothecin and Preparation thereof Each 15 ampoules of the lyophilized preparation has a prescription composition of:

| | |
|---|---|
| Y-type polyethylene glycol-glutamate glycine pentapeptide-7-ethyl-10-hydroxycamptothecin | 6.945 g |
| Hydrochloric acid | Appropriate amount |
| Water for injection | Added to 90 mL |

Preparation process: a prescription amount of the Y-type polyethylene glycol-glutamate glycine pentapeptide-7-ethyl-10-hydroxycamptothecin was taken, and was added with 80 mL of water for injection, and stirred for 0.5 hour to make the solution completely dissolved, and the pH was adjusted to 3.4 to 3.6 with 1.0% hydrochloric acid, and water for injection was added to full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 20

Lyophilized Preparation of Four-branched Polyethylene Glycol (with a Molecular Weight of 40,000 Daltons)-glutamate Glycine Icosapeptide-7-ethyl-10-hydroxycamptothecin and Preparation thereof Each 15 ampoules of the lyophilized preparation has a prescription composition of:

| | |
|---|---|
| Four-branched polyethylene glycol-glutamate glycine icosapeptide-7-ethyl-10-hydroxycamptothecin | 1.935 g |
| Hydrochloric acid | Appropriate amount |
| Water for injection | Added to 90 mL |

Preparation process: a prescription amount of the four-branched polyethylene glycol-glutamate glycine icosapeptide-7-ethyl-10-hydroxycamptothecin was taken, and was added with 80 mL of water for injection, and stirred for 0.5 hour to make the solution completely dissolved, and the pH was adjusted to 3.4 to 3.6 with 1.0% hydrochloric acid, and water for injection was added to full dose. The solution obtained was filtered through a 0.22 μm microporous filtering film, and subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

EXAMPLE 21

Study on Scale-up of Preparation Process

1. Sample Preparation

A pharmaceutical composition of straight-chain polyethylene glycol-glutamate glutamate pentapeptide-irinotecan for injection was prepared in the pilot production workshop according to the following process, with batch number of 120801, 120901, 121001 and 121201, respectively.

(1) Prescription:

| | |
|---|---|
| Straight-chain polyethylene glycol-glutamate glutamate pentapeptide-irinotecan | 285 g |
| Hydrochloric acid | Appropriate amount (the pH was adjusted to 3.4 to 3.6) |
| Water for injection | Added to 6000 ml |
| Production | 1000 ampoules |

(2) Preparation Method:

285 g of the straight-chain polyethylene glycol-glutamate glycine icosapeptide-irinotecan was weighed, and was added with 90% of prescription amount of water for injection, and stirred to make the solution completely dissolved, and the pH was adjusted to 3.4 to 3.6 with hydrochloric acid, and water for injection was added to full dose. The solution obtained was subpackaged according to 6 ml/ampoule in the 100-class clean area, and pre-frozen at −40° C. for 4 to 8 hours, followed by being subjected to sublimation drying completed within 40 to 60 hours, and finally desorption drying at 25° C. for 4 to 8 hours, and plugged under vacuum and capped.

2. Impact Factor Test

The 120801 batch samples were taken for impact factor test, and test conditions were high temperature 60° C., high temperature 40° C., high humidity (RH92.5%) and strong light irradiation (4500Lx).

(1) Light Test

In a light cabinet at room temperature and with an intensity of illumination of 4500Lx, the samples with external packing and without external packing were placed at the same time for 10 days, and sampled at $5^{th}$ and $10^{th}$ day for various inspections, and the results are shown in Table 6.

TABLE 6

| | | | | | Insoluble particles (grain/ampoule) | | Visible foreign |
|---|---|---|---|---|---|---|---|
| Time (day) | Placement condition | Character | pH value | Moisture | ≥10 um | ≥25 um | matter |
| 0 | Random | Light yellow loose block | 3.48 | 1.26% | 965 | 7 | 1, 0, 0, 1, 1 |
| 5 | Without external packing | Dark yellow loose block | 3.11 | 1.34% | — | — | 1, 0, 0, 0, 0 |
| | With external packing | Light yellow loose block | 3.62 | 1.37% | 1243 | 28 | 0, 1, 0, 0, 0 |

TABLE 6-continued

| | | | | | | | |
|---|---|---|---|---|---|---|---|
| 10 | Without external packing | Tan loose block | 3.02 | 1.40% | — | — | 0, 0, 0, 0, 0 |
| | With external packing | Light yellow loose block | 3.78 | 1.41% | 778 | 22 | 0, 0, 0, 0, 1 |

Investigation results of light test (2)

| | | Osmotic pressure (mOsmol · kg$^{-1}$) | | | | | |
|---|---|---|---|---|---|---|---|
| | | 0.9% Sodium chloride | | Glucose for injection | | Solution | |
| Time (day) | Placement condition | 10 mg/ml | 30 mg/ml | 10 mg/ml | 30 mg/ml | clarity | Solution color |
| 0 | Random | 290 | 308 | 276 | 304 | Equal to No. 1 | Lighter than Yellow No. 1 |
| 5 | Without external packing | 288 | 306 | 278 | 304 | Lighter than No. 1 | Lighter than Yellow No. 3 |
| | With external packing | 288 | 304 | 279 | 305 | Lighter than No. 1 | Lighter than Yellow No. 1 |
| 10 | Without external packing | 290 | 308 | 276 | 305 | Lighter than No. 1 | Lighter than Yellow No. 5 |
| | With external packing | 290 | 306 | 278 | 306 | Lighter than No. 1 | Lighter than Yellow No. 1 |

Investigation results of light test (3)

| | | Small molecule related substances (ppm) | | | Macromolecule related substances (%) | | | |
|---|---|---|---|---|---|---|---|---|
| | | | Maximum | | | | | |
| Time (day) | Placement condition | Irinotecan | individual impurity | Total impurity | Disubstituted | Single substituted | Free PEG | Content (%) |
| 0 | Random | 11.94 | 33.60 | 73.93 | 6.99 | 0.58 | 1.28 | 99.26 |
| 5 | Without external packing | 34.78 | 1689.97 | 2612.60 | 16.33 | 2.55 | 3.17 | 67.76 |
| | With external packing | 25.35 | 37.91 | 113.14 | 7.27 | 0.68 | 1.44 | 99.52 |
| 10 | Without external packing | 42.13 | 2289.93 | 3538.04 | 15.81 | 2.83 | 3.29 | 73.23 |
| | With external packing | 10.57 | 24.37 | 97.96 | 7.21 | 0.73 | 1.60 | 100.24 |

The results show that: (1) the product is very sensitive to light, and must be sealed and kept shading for preservation; (2) in the designed packaging conditions, after light test, the appearance character, pH, moisture, visible foreign matter, insoluble particles, solution clarity and color have no significant change compared with those at $0^{th}$ day, and both the related substances and content detection have no significant change.

(2) High Temperature Test

The product was taken, removed the external packing, and placed under 40° C. condition for 10 days, and sampled at 5th and 10th day for various inspections, and the results are shown in Table 7.

TABLE 7

Investigation results of high temperature test (1)

| | | | | Insoluble particles (grain/ampoule) | | Visible foreign |
|---|---|---|---|---|---|---|
| Time (day) | Character | pH value | Moisture | ≥10 um | ≥25 um | matter |
| 0 | Light yellow loose block | 3.48 | 1.26% | 965 | 7 | 1, 0, 0, 1, 1 |
| 5 | Light yellow loose block | 3.42 | 1.35% | 1072 | 110 | 0, 1, 0, 0, 0 |

TABLE 7-continued

| | | | | | | |
|---|---|---|---|---|---|---|
| 10 | Light yellow loose block | 3.33 | 1.34% | 996 | 3 | 2, 0, 0, 0, 0 |

Investigation results of high temperature test (2)

| Time (day) | Osmotic pressure (mOsmol · kg⁻¹) | | | | Solution clarity | Solution color |
|---|---|---|---|---|---|---|
| | 0.9% Sodium chloride | | Glucose for injection | | | |
| | 10 mg/ml | 30 mg/ml | 10 mg/ml | 30 mg/ml | | |
| 0 | 290 | 308 | 276 | 304 | Equal to No. 1 | Lighter than Yellow No. 1 |
| 5 | 290 | 310 | 279 | 304 | Lighter than No. 1 | Lighter than Yellow No. 1 |
| 10 | 291 | 308 | 278 | 308 | Lighter than No. 1 | Lighter than Yellow No. 1 |

Investigation results of high temperature test (3)

| Time (day) | Small molecule related substances(ppm) | | Macromolecule related substances(%) | | | Content (%) |
|---|---|---|---|---|---|---|
| | Irinotecan | Maximum individual impurity | Total impurity | Disubstituted | Single substituted | Free PEG |
| 0 | 11.94 | 33.60 | 73.93 | 6.99 | 0.58 | 1.28 | 99.26 |
| 5 | 16.34 | 38.88 | 136.64 | 7.51 | 0.71 | 1.93 | 99.41 |
| 10 | 10.82 | 115.47 | 182.91 | 7.64 | 0.77 | 2.05 | 99.42 |

The results show that: after high temperature test, the appearance character, pH, moisture, visible foreign matter, osmotic pressure, insoluble particles, solution clarity and color, content of the product have no significant change compared with those at $0^{th}$ day, and the small molecule, macromolecule related substances are slightly increased, indicating that the product is sensitive to heat, and should be kept cold for preservation.

(3) High Humidity Test

The product was taken, removed the external packing, and placed under the condition of a high humidity (RH92.5%, T=25° C.) for 10 days, and sampled at $5^{th}$ and $10^{th}$ day for various inspections, and the results are shown in Table 8.

TABLE 8

Investigation results of high humidity test (1)

| Time (day) | Character | pH value | Moisture | Insoluble particles (grain/ampoule) | | Visible foreign matter |
|---|---|---|---|---|---|---|
| | | | | ≥10 um | ≥25 um | |
| 0 | Light yellow loose block | 3.48 | 1.26% | 965 | 7 | 1, 0, 0, 1, 1 |
| 5 | Light yellow loose block | 3.87 | 1.58% | 780 | 12 | 2, 0, 0, 0, 0 |
| 10 | Light yellow loose block | 3.96 | 1.60% | 1483 | 25 | 0, 3, 0, 0, 0 |

Investigation results of high humidity test (2)

| Time (day) | Osmotic pressure (mOsmol · kg-1) | | | | Solution clarity | Solution color |
|---|---|---|---|---|---|---|
| | 0.9% Sodium chloride | | Glucose for injection | | | |
| | 10 mg/ml | 30 mg/ml | 10 mg/ml | 30 mg/ml | | |
| 0 | 290 | 308 | 276 | 304 | Equal to No. 1 | Lighter than Yellow No. 1 |
| 5 | 290 | 306 | 276 | 306 | Lighter than No. 1 | Lighter than Yellow No. 1 |
| 10 | 288 | 309 | 274 | 304 | Lighter than No. 2 | Lighter than Yellow No. 1 |

TABLE 8-continued

Investigation results of high humidity test (3)

| Time (day) | Small molecule related substances (ppm) | | | Macromolecule related substances (%) | | | |
|---|---|---|---|---|---|---|---|
| | Irinotecan | Maximum individual impurity | Total impurity | Disubstituted | Single substituted | Free PEG | Content (%) |
| 0 | 11.94 | 33.60 | 73.93 | 6.99 | 0.58 | 1.28 | 99.26 |
| 5 | 21.05 | 40.38 | 115.64 | 7.77 | 0.74 | 1.96 | 100.38 |
| 10 | 11.04 | 25.32 | 111.07 | 7.33 | 0.72 | 2.18 | 100.12 |

The results show that: after high humidity test, the appearance character, pH, moisture, visible foreign matter, osmotic pressure, insoluble particles, solution clarity and color, related substances, content of the product have no significant change compared with those at $0^{th}$ day, indicating that the product is not sensitive to humidity.

3. Compatibility Stability Test

The 120801 batch samples were taken, and the compatibility of the sample and 0.9% sodium chloride injection and 5% glucose injection, respectively, were investigated, and sampled at $0^{th}$, $2^{nd}$, $4^{th}$, $8^{th}$ hour for the detection of small molecule related substances, and the results shown in Table 9.

TABLE 9

Change of related substances in compatibility at different time

| Time (h) | Compatibility of the sample and sodium chloride injection (ppm) | | | Compatibility of the sample and glucose injection (ppm) | | |
|---|---|---|---|---|---|---|
| | Irinotecan | Maximum individual impurity | Total impurity | Irinotecan | Maximum individual impurity | Total impurity |
| 0 | 3.60 | 19.32 | 73.76 | 4.11 | 27.00 | 101.63 |
| 1 | 5.97 | 26.63 | 83.51 | 5.90 | 47.04 | 115.17 |
| 2 | 8.04 | 26.19 | 88.83 | 8.08 | 46.67 | 123.49 |
| 4 | 10.07 | 20.76 | 97.18 | 11.56 | 38.59 | 134.94 |
| 8 | 16.43 | 20.04 | 107.56 | 16.31 | 48.57 | 134.79 |

In the compatibility test of the sample and 0.9% sodium chloride injection and 5% glucose injection, respectively, the product has a good stability within 8 hours.

4. Acceleration Test

The samples with packing were placed in a constant temperature and humidity chamber at a temperature of 25° C.±2° C. and a relative humidity of 60%±10% for 6 months, and sampled at $1^{st}$, $2^{nd}$, $3^{rd}$, $6^{th}$ month, respectively, for various inspections; and the sample at $6^{th}$ month was taken for bacterial endotoxin and sterile examination. The accelerated test results are shown in Table 10, 11, 12.

TABLE 10

Acceleration test results of the 120901 batch preparation sample (1)

| Time (month) | Placement condition | Character | pH value | Moisture | Insoluble particles (grain/ampoule) ≥10 um | Insoluble particles (grain/ampoule) ≥25 um | Visible foreign matter |
|---|---|---|---|---|---|---|---|
| 0 | Random | Yellow loose block | 3.54 | 1.18% | 2627 | 30 | 1, 0, 0, 0, 0 |
| 1 | Random | Yellow loose block | 3.71 | 1.07% | 3363 | 20 | 0, 0, 0, 0, 0 |
| 2 | Random | Yellow loose block | 3.67 | 1.21% | 2665 | 0 | 0, 1, 1, 0, 0 |
| 3 | Placed forward | Yellow loose block | 3.71 | 1.15% | 2208 | 22 | 2, 0, 0, 0, 0 |
| | Placed upside down | Yellow loose block | 3.63 | 1.16% | 2053 | 30 | 0, 0, 1, 0, 1 |
| 6 | Placed forward | Yellow loose block | 3.70 | 1.23% | 2600 | 15 | 0, 0, 0, 0, 2 |
| | Placed upside down | Yellow loose block | 3.73 | 1.20% | 2648 | 25 | 0, 1, 0, 0, 0 |

TABLE 10-continued

Acceleration test results of the 120901 batch preparation sample (2)

| Time (month) | Placement condition | Osmotic pressure (mOsmol · kg$^{-1}$) | | | | Solution clarity | Solution color | Sterile | Bacterial endotoxin (EU/mg) |
| --- | --- | --- | --- | --- | --- | --- | --- | --- | --- |
| | | 0.9% Sodium chloride | | Glucose for injection | | | | | |
| | | 10 mg/ml | 30 mg/ml | 10 mg/ml | 30 mg/ml | | | | |
| 0 | Random | 294 | 308 | 272 | 302 | Equal to No. 2 | Lighter than Yellow No. 2 | The examination at 0$^{th}$, 6$^{th}$ month conformed to the regulations. | 0$^{th}$ month: 0.006; 6$^{th}$ month: <0.004 |
| 1 | Random | 293 | 306 | 272 | 304 | | | | |
| 2 | Random | 296 | 308 | 274 | 301 | | | | |
| 3 | Placed forward | 295 | 310 | 274 | 300 | | | | |
| | Placed upside down | 296 | 306 | 275 | 306 | | | | |
| 6 | Placed forward | 296 | 306 | 276 | 301 | | | | |
| | Placed upside down | 294 | 309 | 276 | 306 | | | | |

Acceleration test results of the 120901 batch preparation sample (3)

| Time | Placement condition | Small molecule related substances (ppm) | | | Macromolecule related substances (%) | | | Content (%) |
| --- | --- | --- | --- | --- | --- | --- | --- | --- |
| | | Irinotecan | Maximum individual impurity | Total impurity | Disubstituted | Single substituted | Free PEG | |
| Month 0 | Random | 6.64 | 17.99 | 52.30 | 7.76 | 0.70 | 1.35 | 101.9 |
| Month 1 | Random | 11.17 | 19.51 | 70.48 | 7.41 | 0.84 | 1.27 | 100.8 |
| Month 2 | Random | 7.26 | 22.37 | 104.9 | 7.52 | 0.63 | 1.13 | 101.8 |
| Month 3 | Placed forward | 11.01 | 23.54 | 103.7 | 7.14 | 0.64 | 1.09 | 101.7 |
| | Placed upside down | 13.48 | 32.88 | 124.6 | 7.08 | 0.55 | 1.13 | 102.1 |
| Month 6 | Placed forward | 14.74 | 21.17 | 119.8 | 7.24 | 0.69 | 1.29 | 102.0 |
| | Placed upside down | 17.52 | 27.20 | 108.7 | 7.41 | 0.79 | 1.36 | 101.5 |

TABLE 11

Acceleration test results of the 121001 batch preparation sample (1)

| Time (month) | Placement condition | Character | pH value | Moisture | Insoluble particles (grain/ampoule) | | Visible foreign matter |
| --- | --- | --- | --- | --- | --- | --- | --- |
| | | | | | ≥10 um | ≥25 um | |
| 0 | Random | Yellow loose block | 3.50 | 1.22% | 738 | 38 | 1, 2, 0, 0, 0 |
| 1 | Random | Yellow loose block | 3.63 | 1.12% | 728 | 7 | 1, 0, 0, 0, 0 |
| 2 | Random | Yellow loose block | 3.66 | 1.18% | 653 | 5 | 0, 0, 0, 1, 0 |
| 3 | Placed forward | Yellow loose block | 3.61 | 1.24% | 592 | 3 | 0, 0, 2, 0, 1 |
| | Placed upside down | Yellow loose block | 3.58 | 1.23% | 950 | 5 | 0, 0, 0, 0, 1 |
| 6 | Placed forward | Yellow loose block | 3.65 | 1.25% | 922 | 8 | 0, 0, 1, 1, 0 |

TABLE 11-continued

|  | Placed upside down | Yellow loose block | 3.63 | 1.24% | 773 | 13 | 1, 0, 0, 0, 0 |

Acceleration test results of the 121001 batch preparation sample (2)

| | | Osmotic pressure (mOsmol · kg$^{-1}$) | | | | | | | |
|---|---|---|---|---|---|---|---|---|---|
| | | 0.9% Sodium chloride | | Glucose for injection | | | | | Bacterial |
| Time (month) | Placement condition | 10 mg/ml | 30 mg/ml | 10 mg/ml | 30 mg/ml | Solution clarity | Solution color | Sterile | endotoxin (EU/mg) |
| 0 | Random | 292 | 303 | 276 | 302 | Lighter than No. 1 | Lighter than Yellow No. 2 | The examination at 0$^{th}$, 6$^{th}$ month conformed to the regulations. | 0$^{th}$ month: 0.015; 6$^{th}$ month: <0.004 |
| 1 | Random | 291 | 306 | 274 | 302 | | | | |
| 2 | Random | 294 | 302 | 277 | 306 | | | | |
| 3 | Placed forward | 294 | 304 | 274 | 302 | | | | |
| | Placed upside down | 292 | 305 | 277 | 306 | | | | |
| 6 | Placed forward | 296 | 302 | 278 | 306 | | | | |
| | Placed upside down | 293 | 306 | 276 | 305 | | | | |

Acceleration test results of the 121001 batch preparation sample (3)

| | | Small molecule related substances (ppm) | | | Macromolecule related substances (%) | | | |
|---|---|---|---|---|---|---|---|---|
| Time | Placement condition | Irinotecan | Maximum individual impurity | Total impurity | Disubstituted | Single substituted | Free PEG | Content (%) |
| Month 0 | Random | 4.21 | 19.34 | 47.49 | 7.51 | 0.81 | 1.17 | 102.4 |
| Month 1 | Random | 11.95 | 19.66 | 66.96 | 7.66 | 0.80 | 1.35 | 101.3 |
| Month 2 | Random | 4.90 | 25.60 | 99.55 | 7.38 | 0.67 | 1.53 | 101.4 |
| Month 3 | Placed forward | 14.11 | 21.44 | 172.8 | 7.57 | 0.73 | 1.27 | 102.6 |
| | Placed upside down | 11.37 | 73.78 | 128.0 | 7.70 | 0.71 | 1.47 | 102.0 |
| Month 6 | Placed forward | 16.60 | 17.80 | 110.2 | 7.55 | 0.79 | 1.49 | 102.4 |
| | Placed upside down | 4.21 | 19.34 | 47.49 | 7.51 | 0.81 | 1.17 | 102.4 |

TABLE 12

Acceleration test results of the 121201 batch preparation sample (1)

| | | | | | Insoluble particles (grain/ampoule) | | Visible |
|---|---|---|---|---|---|---|---|
| Time (month) | Placement condition | Character | pH value | Moisture | ≥10 um | ≥25 um | foreign matter |
| 0 | Random | Yellow loose block | 3.43 | 1.15% | 1838 | 2 | 1, 1, 0, 0, 0 |
| 1 | Random | Yellow loose block | 3.55 | 1.17% | 1967 | 30 | 0, 1, 0, 1, 0 |
| 2 | Random | Yellow loose block | 3.62 | 1.14% | 1853 | 43 | 0, 0, 0, 1, 0 |
| 3 | Placed forward | Yellow loose block | 3.71 | 1.20% | 1108 | 8 | 1, 0, 0, 0, 0 |
| | Placed upside down | Yellow loose block | 3.62 | 1.21% | 1213 | 15 | 0, 0, 0, 0, 2 |

TABLE 12-continued

| | | | | | | | | |
|---|---|---|---|---|---|---|---|---|
| 6 | Placed forward | Yellow loose block | 3.59 | 1.19% | 933 | 2 | | 0, 0, 0, 0, 1 |
| | Placed upside down | Yellow loose block | 3.72 | 1.20% | 975 | 8 | | 0, 0, 1, 1, 0 |

Acceleration test results of the 121201 batch preparation sample (2)

| | | Osmotic pressure (mOsmol · kg$^{-1}$) | | | | | | | |
|---|---|---|---|---|---|---|---|---|---|
| | | 0.9% Sodium chloride | | Glucose for injection | | | | | Bacterial |
| Time (month) | Placement condition | 10 mg/ml | 30 mg/ml | 10 mg/ml | 30 mg/ml | Solution clarity | Solution color | Sterile | endotoxin (EU/mg) |
| 0 | Random | 295 | 308 | 275 | 305 | Lighter than No. 1 | Lighter than Yellow No. 2 | The examination at 0$^{th}$, 6$^{th}$ month conformed to the regulations. | 0$^{th}$ month: <0.004; 6$^{th}$ month: <0.004 |
| 1 | Random | 296 | 310 | 277 | 302 | | | | |
| 2 | Random | 293 | 308 | 274 | 306 | | | | |
| 3 | Placed forward | 295 | 306 | 274 | 305 | | | | |
| | Placed upside down | 294 | 306 | 279 | 308 | | | | |
| 6 | Placed forward | 294 | 305 | 276 | 306 | | | | |
| | Placed upside down | 294 | 308 | 278 | 307 | | | | |

Acceleration test results of the 121201 batch preparation sample (3)

| | | Small molecule related substances (ppm) | | | Macromolecule related substances (%) | | | |
|---|---|---|---|---|---|---|---|---|
| | | | Maximum individual impurity | Total impurity | | | Free PEG | Content (%) |
| Time | Placement condition | Irinotecan | | | Disubstituted | Single substituted | | |
| Month 0 | Random | 5.32 | 17.37 | 43.07 | 7.59 | 0.68 | 1.47 | 103.6 |
| Month 1 | Random | 16.88 | 19.87 | 87.95 | 7.83 | 0.65 | 1.80 | 102.6 |
| Month 2 | Random | 9.34 | 26.14 | 97.29 | 7.59 | 0.67 | 1.65 | 103.1 |
| Month 3 | Placed forward | 13.83 | 23.41 | 130.1 | 7.57 | 0.74 | 1.85 | 103.5 |
| | Placed upside down | 15.83 | 25.29 | 131.9 | 7.79 | 0.70 | 2.00 | 103.3 |
| Month 6 | Placed forward | 13.68 | 21.15 | 126.7 | 7.41 | 0.68 | 1.50 | 103.6 |
| | Placed upside down | 18.04 | 22.11 | 139.9 | 7.50 | 0.69 | 1.45 | 103.6 |

In the investigation of acceleration test for 6 months, the appearance character, pH, moisture, visible foreign matter, osmotic pressure, insoluble particles, solution clarity and color, macromolecule related substances, content of the product have no significant change, small molecule related substances, the total impurity are slightly increased, but are within the limits, the product is stable in the conditions.

5. Long-Term Test

The preparation samples were placed in a constant temperature and humidity chamber at a temperature of 4 to 8° C., forward and overturned, respectively, for 12 months, and sampled at 0$^{st}$, 3$^{rd}$, 6$^{th}$, 9$^{th}$, 12$^{th}$ month, respectively, for various inspections, and the sample at 12$^{th}$ month was taken for bacterial endotoxin and sterile examination. The long-term test results are shown in Table 13, 14, 15.

TABLE 13

Long-term test results of the 120901 batch preparation sample (1)

| Time (month) | Placement condition | Character | pH value | Moisture | Insoluble particles (grain/ampoule) ≥10 um | Insoluble particles (grain/ampoule) ≥25 um | Visible foreign matter |
|---|---|---|---|---|---|---|---|
| 0 | Random | Yellow loose block | 3.54 | 1.18% | 2627 | 30 | 1, 0, 0, 0, 0 |
| 3 | Placed forward | Yellow loose block | 3.70 | 1.17% | 3285 | 57 | 1, 0, 0, 0, 0 |
|   | Placed upside down | Yellow loose block | 3.68 | 1.15% | 2498 | 7 | 0, 0, 0, 0, 0 |
| 6 | Placed forward | Yellow loose block | 3.76 | 1.12% | 2063 | 10 | 0, 0, 0, 0, 0 |
|   | Placed upside down | Yellow loose block | 3.71 | 1.13% | 2638 | 35 | 0, 2, 0, 0, 0 |
| 9 | Random | Yellow loose block | 3.63 | 1.19% | 1835 | 0 | 0, 2, 0, 0, 0 |
| 12 | Placed forward | Yellow loose block | 3.66 | 1.16% | 1923 | 42 | 0, 0, 0, 1, 1 |
|   | Placed upside down | Yellow loose block | 3.59 | 1.18% | 1507 | 53 | 1, 0, 0, 0, 1 |

Long-term test results of the 120901 batch preparation sample (2)

| Time (month) | Placement condition | Osmotic pressure (mOsmol·kg$^{-1}$) 0.9% Sodium chloride 10 mg/ml | Osmotic pressure (mOsmol·kg$^{-1}$) 0.9% Sodium chloride 30 mg/ml | Osmotic pressure (mOsmol·kg$^{-1}$) Glucose for injection 10 mg/ml | Osmotic pressure (mOsmol·kg$^{-1}$) Glucose for injection 30 mg/ml | Solution clarity | Solution color | Sterile | Bacterial endotoxin (EU/mg) |
|---|---|---|---|---|---|---|---|---|---|
| 0 | Random | 294 | 308 | 272 | 302 | Equal to No. 2 | Lighter than Yellow No. 2 | The examination at 0th, 12th month conformed to the regulations. | 0$^{th}$ month: 0.006 12$^{th}$ month: <0.004 |
| 3 | Placed forward | 291 | 308 | 274 | 304 | | | | |
|   | Placed upside down | 295 | 306 | 276 | 304 | | | | |
| 6 | Placed forward | 296 | 304 | 274 | 300 | | | | |
|   | Placed upside down | 294 | 310 | 276 | 304 | | | | |
| 9 | Random | 294 | 307 | 274 | 304 | | | | |
| 12 | Placed forward | 296 | 305 | 276 | 300 | | | | |
|   | Placed upside down | 294 | 307 | 278 | 306 | | | | |

Long-term test results of the 120901 batch preparation sample (3)

| Time | Placement condition | Small molecule related substances (ppm) Irinotecan | Small molecule related substances (ppm) Maximum individual impurity | Small molecule related substances (ppm) Total impurity | Macromolecule related substances (%) Disubstituted | Macromolecule related substances (%) Single substituted | Free PEG | Content (%) |
|---|---|---|---|---|---|---|---|---|
| Month 0 | Random | 6.64 | 17.99 | 52.30 | 7.76 | 0.70 | 1.35 | 101.9 |
| Month 3 | Placed forward | 8.83 | 22.75 | 89.79 | 6.64 | 0.56 | 0.89 | 102.0 |
|   | Placed upside down | 9.67 | 22.88 | 89.93 | 7.15 | 0.55 | 0.98 | 102.4 |
| Month 6 | Placed forward | 12.82 | 22.20 | 95.05 | 7.26 | 0.81 | 1.18 | 101.2 |
|   | Placed upside down | 13.73 | 24.01 | 96.13 | 7.39 | 0.78 | 1.24 | 102.5 |
| Month 9 | Random | 10.17 | 58.54 | 114.6 | 7.19 | 0.84 | 1.05 | 100.8 |

TABLE 13-continued

| Month 12 | Placed forward | 11.32 | 18.97 | 126.2 | 7.12 | 0.77 | 1.14 | 102.5 |
| | Placed upside down | 12.03 | 17.09 | 109.5 | 7.08 | 0.76 | 1.17 | 102.1 |

TABLE 14

Long-term test results of the 121001 batch preparation sample (1)

| Time (month) | Placement condition | Character | pH value | Moisture | Insoluble particles (grain/ampoule) ≥10 um | Insoluble particles (grain/ampoule) ≥25 um | Visible foreign matter |
|---|---|---|---|---|---|---|---|
| 0 | Random | Yellow loose block | 3.50 | 1.22% | 738 | 38 | 1, 2, 0, 0, 0 |
| 3 | Placed forward | Yellow loose block | 3.65 | 1.15% | 1118 | 5 | 0, 1, 1, 1, 0 |
|   | Placed upside down | Yellow loose block | 3.59 | 1.14% | 948 | 13 | 0, 0, 0, 0, 0 |
| 6 | Placed forward | Yellow loose block | 3.58 | 1.21% | 997 | 60 | 0, 1, 0, 0, 0 |
|   | Placed upside down | Yellow loose block | 3.60 | 1.20% | 858 | 28 | 0, 0, 0, 0, 0 |
| 9 | Random | Yellow loose block | 3.54 | 1.19% | 998 | 7 | 1.0, 01, 1 |
| 12 | Placed forward | Yellow loose block | 3.53 | 1.23% | 1360 | 30 | 1, 0, 0, 0, 1 |
| 12 | Placed upside down | Yellow loose block | 3.59 | 1.21% | 847 | 7 | 0, 1, 0, 0, 0 |

Long-term test results of the 121001 batch preparation sample (2)

| Time (month) | Placement condition | Osmotic pressure (mOsmol · kg$^{-1}$) 0.9% Sodium chloride 10 mg/ml | Osmotic pressure (mOsmol · kg$^{-1}$) 0.9% Sodium chloride 30 mg/ml | Osmotic pressure (mOsmol · kg$^{-1}$) Glucose for injection 10 mg/ml | Osmotic pressure (mOsmol · kg$^{-1}$) Glucose for injection 30 mg/ml | Solution clarity | Solution color | Sterile | Bacterial endotoxin (EU/mg) |
|---|---|---|---|---|---|---|---|---|---|
| 0 | Random | 292 | 303 | 276 | 302 | Lighter than No. 1 | Lighter than Yellow No. 2 | The examination at 0th, 12th month conformed to the regulations. | 0$^{th}$ month: 0.015 12$^{th}$ month: <0.004 |
| 3 | Placed forward | 291 | 306 | 275 | 300 | | | | |
|   | Placed upside down | 292 | 308 | 278 | 304 | | | | |
| 6 | Placed forward | 292 | 303 | 274 | 304 | | | | |
|   | Placed upside down | 296 | 309 | 279 | 306 | | | | |
| 9 | Random | 292 | 305 | 278 | 304 | | | | |
| 12 | Placed forward | 293 | 302 | 276 | 306 | | | | |
|   | Placed upside down | 296 | 306 | 276 | 302 | | | | |

Long-term test results of the 121001 batch preparation sample (3)

| Time | Placement condition | Small molecule related substances (ppm) Irinotecan | Small molecule related substances (ppm) Maximum individual impurity | Small molecule related substances (ppm) Total impurity | Macromolecule related substances (%) Disubstituted | Macromolecule related substances (%) Single substituted | Free PEG | Content (%) |
|---|---|---|---|---|---|---|---|---|
| Month 0 | Random | 4.21 | 19.34 | 47.49 | 7.51 | 0.81 | 1.17 | 102.4 |
| Month 3 | Placed forward | 12.52 | 63.66 | 116.8 | 7.39 | 0.65 | 1.15 | 102.3 |

TABLE 14-continued

|  |  |  |  |  |  |  |  |  |
|---|---|---|---|---|---|---|---|---|
|  | Placed upside down | 15.79 | 62.99 | 125.4 | 7.53 | 0.77 | 1.26 | 102.6 |
| Month 6 | Placed forward | 13.06 | 23.51 | 109.8 | 7.27 | 0.80 | 1.30 | 101.9 |
|  | Placed upside down | 17.15 | 23.02 | 109.3 | 7.17 | 0.77 | 1.28 | 101.8 |
| Month 9 | Random | 8.71 | 37.27 | 124.8 | 7.18 | 0.76 | 1.22 | 100.5 |
| Month 12 | Placed forward | 10.59 | 89.78 | 167.8 | 7.04 | 0.76 | 1.01 | 101.5 |
|  | Placed upside down | 12.96 | 27.67 | 116.0 | 7.23 | 0.86 | 1.21 | 101.0 |

TABLE 15

Long-term test results of the 121201 batch preparation sample (1)

| Time (month) | Placement condition | Character | pH value | Moisture | Insoluble particles (grain/ampoule) ≥10 um | Insoluble particles (grain/ampoule) ≥25 um | Visible foreign matter |
|---|---|---|---|---|---|---|---|
| 0 | Random | Yellow loose block | 3.43 | 1.15% | 1838 | 2 | 1, 1, 0, 0, 0 |
| 3 | Placed forward | Yellow loose block | 3.46 | 1.19% | 1430 | 88 | 0, 1, 1, 0, 0 |
|  | Placed upside down | Yellow loose block | 3.56 | 1.17% | 1090 | 15 | 0, 0, 0, 0, 1 |
| 6 | Placed forward | Yellow loose block | 3.48 | 1.16% | 648 | 2 | 0, 0, 0, 0, 2 |
|  | Placed upside down | Yellow loose block | 3.39 | 1.14% | 792 | 8 | 1, 0, 0, 0, 0 |
| 9 | Random | Yellow loose block | 3.41 | 1.08% | 827 | 0 | 1, 0, 0, 0, 0 |
| 12 | Placed forward | Yellow loose block | 3.55 | 1.17% | 640 | 0 | 1, 2, 0, 0, 0 |
| 12 | Placed upside down | Yellow loose block | 3.59 | 1.18% | 748 | 0 | 0, 0, 0, 0, 0 |

Long-term test results of the 121201 batch preparation sample (2)

| Time (month) | Placement condition | Osmotic pressure (mOsmol·kg$^{-1}$) 0.9% Sodium chloride 10 mg/ml | Osmotic pressure (mOsmol·kg$^{-1}$) 0.9% Sodium chloride 30 mg/ml | Osmotic pressure (mOsmol·kg$^{-1}$) Glucose for injection 10 mg/ml | Osmotic pressure (mOsmol·kg$^{-1}$) Glucose for injection 30 mg/ml | Solution clarity | Solution color | Sterile | Bacterial endotoxin (EU/mg) |
|---|---|---|---|---|---|---|---|---|---|
| 0 | Random | 295 | 308 | 275 | 305 | Lighter than No. 1 | Lighter than Yellow No. 2 | The examination at 0th, 12th month conformed to the regulations. | 0$^{th}$ month <0.004 12$^{th}$ month: <0.004 |
| 3 | Placed forward | 294 | 308 | 274 | 306 |  |  |  |  |
|  | Placed upside down | 294 | 308 | 276 | 304 |  |  |  |  |
| 6 | Placed forward | 296 | 306 | 276 | 304 |  |  |  |  |
|  | Placed upside down | 296 | 306 | 276 | 305 |  |  |  |  |
| 9 | Random | 294 | 309 | 279 | 304 |  |  |  |  |
| 12 | Placed forward | 292 | 306 | 276 | 303 |  |  |  |  |
|  | Placed upside down | 292 | 306 | 275 | 304 |  |  |  |  |

TABLE 15-continued

Long-term test results of the 121201 batch preparation sample (3)

| Time | Placement condition | Small molecule related substances (ppm) Irinotecan | Maximum individual impurity | Total impurity | Macromolecule related substances (%) Disubstituted | Single substituted | Free PEG | Content (%) |
|---|---|---|---|---|---|---|---|---|
| Month 0 | Random | 5.32 | 17.37 | 43.07 | 7.59 | 0.68 | 1.47 | 103.6 |
| Month 3 | Placed forward | 11.56 | 21.67 | 96.98 | 7.74 | 0.67 | 1.94 | 102.8 |
|  | Placed upside down | 13.97 | 26.94 | 107.4 | 7.62 | 0.71 | 2.01 | 102.0 |
| Month 6 | Placed forward | 8.95 | 21.03 | 119.8 | 7.41 | 0.73 | 1.49 | 103.0 |
|  | Placed upside down | 12.11 | 27.11 | 140.38 | 7.36 | 0.72 | 1.47 | 103.5 |
| Month 9 | Random | 11.88 | 21.18 | 132.6 | 7.21 | 0.72 | 1.40 | 102.5 |
| Month 12 | Placed forward | 12.54 | 19.37 | 130.4 | 7.25 | 0.81 | 1.29 | 102.8 |
|  | Placed upside down | 18.38 | 25.39 | 121.6 | 7.18 | 0.72 | 1.40 | 102.2 |

In the investigation of accelerated long-term test for 12 months, the character, pH, moisture, visible foreign matter, osmotic pressure, insoluble particles, solution clarity and color, macromolecule related substances, content of the product have no significant change, small molecule related substances and the total impurity are slightly increased, indicating that the product has a good stability within 12 months.

The invention claimed is:

1. A pharmaceutical composition of a polyethylene glycol-modified camptothecin derivative, being a lyophilized preparation prepared by a preparation process with the following components: a polyethylene glycol-modified camptothecin derivative, pH adjuster and water for injection, the pharmaceutical composition comprises 100 to 500 mg of the polyethylene glycol-modified camptothecin derivative, wherein in the preparation process, the pH value of the water for injection comprising the polyethylene glycol-modified camptothecin derivative is adjusted to the range of 3.0 to 4.0 by the pH adjuster, and then a lyophilized preparation is prepared in accordance with a freeze-drying procedure, wherein:

the polyethylene glycol-modified camptothecin derivative has the structure of general formula (I):

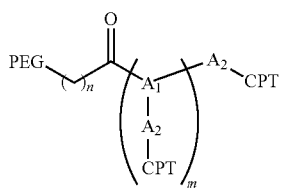

(I)

wherein:

PEG is a straight-chain polyethylene glycol residue having the structure of general formula (II):

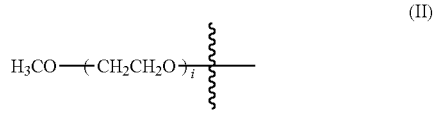

(II)

or, PEG is a Y-type polyethylene glycol residue having the structure of general formula (III):

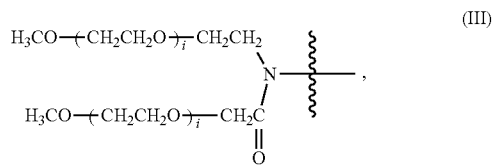

(III)

PEG has a molecular weight of 300 to 60,000 Daltons;

wherein I is an integer of 10 to 1,500

$A_1$ is aspartic acid residue

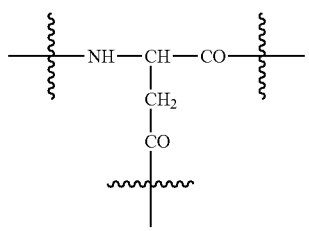 [SMILES: *NC(CC(*)=O)C(*)=O]

or glutamic acid residue

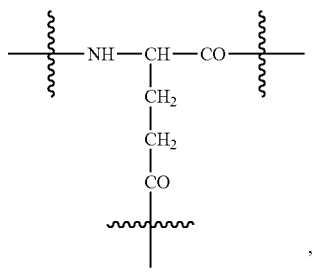 [SMILES: *NC(CCC(*)=O)C(*)=O]

A$_2$ is selected from the group consisting of glycine residue

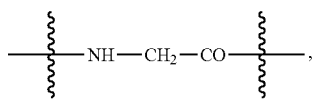

alanine residue

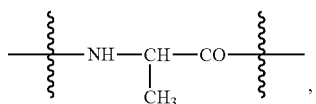

leucine residue

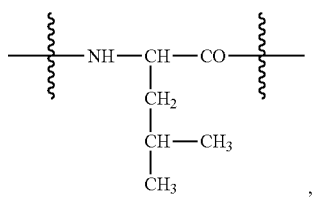 [SMILES: *NC(CC(C)C)C(*)=O]

isoleucine residue

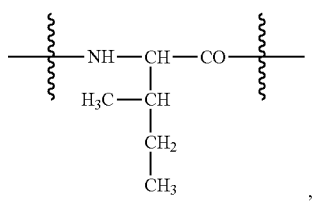

valine residue

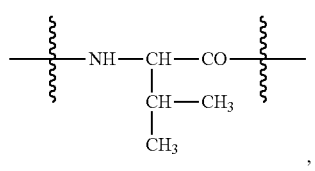 [SMILES: *NC(C(*)=O)C(C)C]

phenylalanine residue

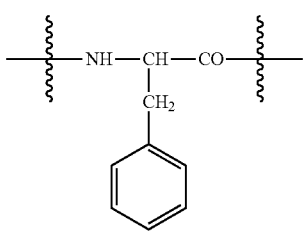 [SMILES: *NC(Cc1ccccc1)C(*)=O]

and methionine residue

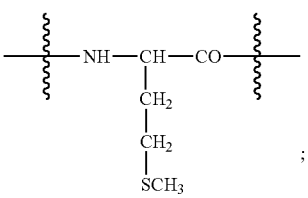 [SMILES: *NC(CCSC)C(*)=O]

m is an integer of 2 to 12;

n is an integer of 0 to 6;

and CPT is a camptothecin derivative residue selected from the group consisting of: 10-hydroxycamptothecin residue

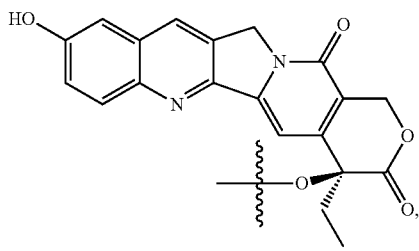 [SMILES: *O[C@]1(CC)C(=O)OCc2c1cc1n(c2=O)Cc2cc3cc(O)ccc3nc2-1]

7-ethyl-10-hydroxycamptothecin residue

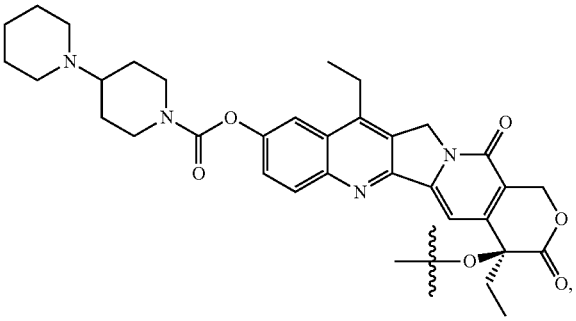 [SMILES: *O[C@]1(CC)C(=O)OCc2c1cc1n(c2=O)Cc2c-1nc1ccc(OC(=O)N3CCC(N4CCCCC4)CC3)cc1c2CC]

45
9-nitrocamptothecin residue
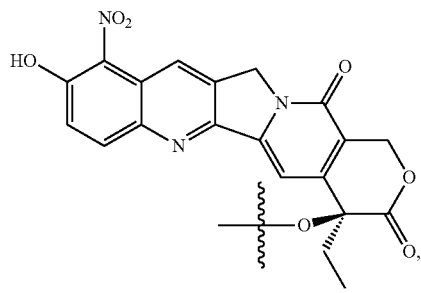 [SMILES: *O[C@]1(CC)C(=O)OCc2c1cc1n(c2=O)Cc2cc3c([N+](=O)[O-])c(O)ccc3nc2-1]
9-aminocamptothecin residue
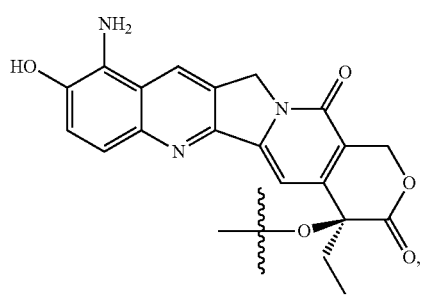 [SMILES: *O[C@]1(CC)C(=O)OCc2c1cc1n(c2=O)Cc2cc3c(N)c(O)ccc3nc2-1]
irinotecan residue
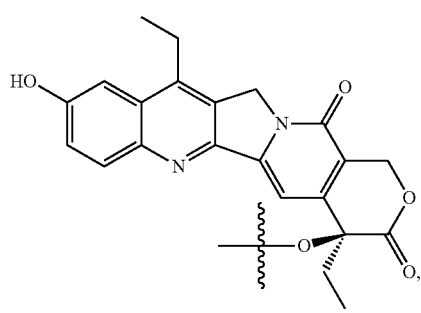 [SMILES: *O[C@]1(CC)C(=O)OCc2c1cc1n(c2=O)Cc2c-1nc1ccc(O)cc1c2CC]
topotecan residue
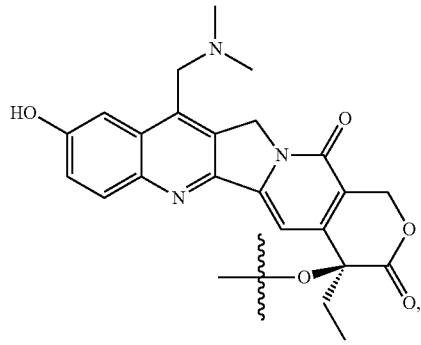 [SMILES: *O[C@]1(CC)C(=O)OCc2c1cc1n(c2=O)Cc2c-1nc1ccc(O)cc1c2CN(C)C]
46
belotecan residue
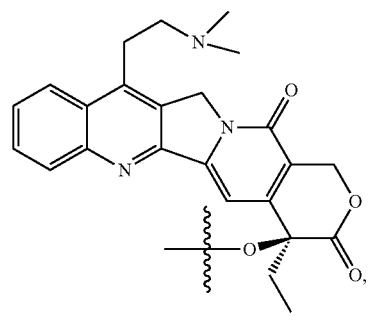 [SMILES: *O[C@]1(CC)C(=O)OCc2c1cc1n(c2=O)Cc2c-1nc1ccccc1c2CCN(C)C]
exatecan residue
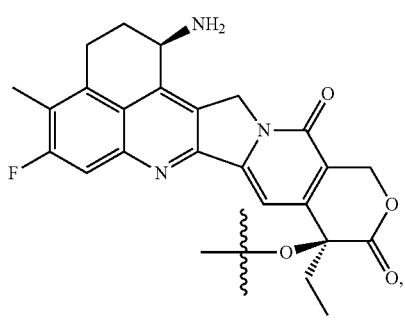 [SMILES: *O[C@]1(CC)C(=O)OCc2c1cc1n(c2=O)Cc2c-1nc1cc(F)c(C)c3c1c2[C@H](N)CC3]
lurtotecan residue
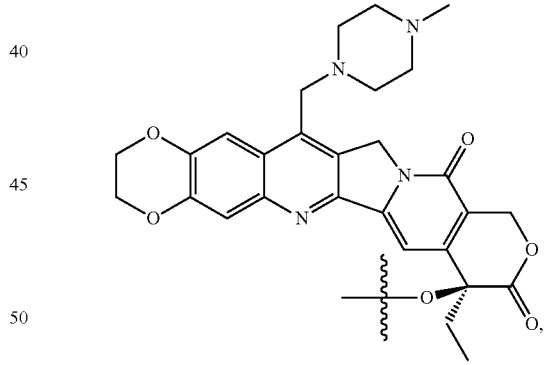
diflomotecan residue
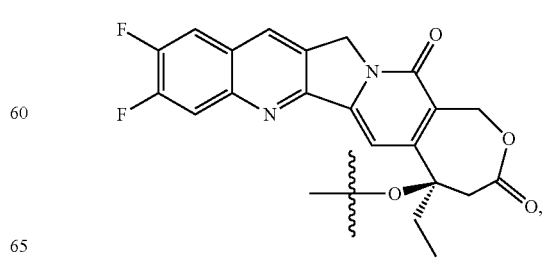

gimatecan residue

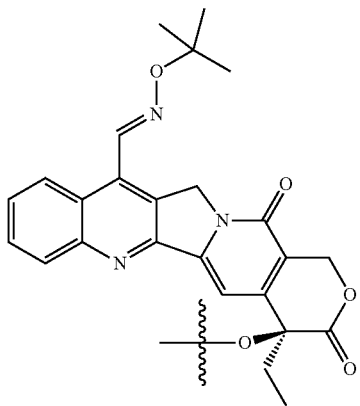 [SMILES: *O[C@]1(CC)C(=O)OCc2c1cc1n(c2=O)Cc2c-1nc1ccccc1c2/C=N/OC(C)(C)C]

and karenitecin residue

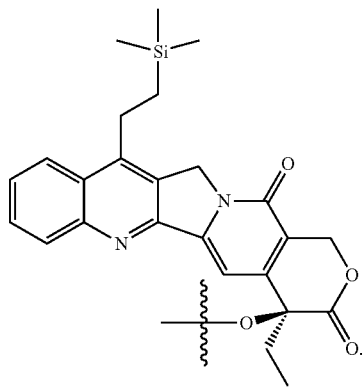 [SMILES: *O[C@]1(CC)C(=O)OCc2c1cc1n(c2=O)Cc2c-1nc1ccccc1c2CC[Si](C)(C)C]

2. The pharmaceutical composition of claim 1, wherein the $A_1$ is glutamic residue acid, the $A_2$ is glycine residue.

3. The pharmaceutical composition of claim 1, wherein the m is 2 to 6.

4. The pharmaceutical composition of claim 1, wherein n is 0, 1, 2 or 3.

5. The pharmaceutical composition of claim 1, wherein the pH adjuster is one or a combination of more than two selected from the group consisting of hydrochloric acid, hydrobromic acid, sulfuric acid, nitric acid, phosphoric acid, carbonic acid, toluenesulfonic acid, methanesulfonic acid, acetic acid, citric acid, malonic acid, tartaric acid, succinic acid, benzoic acid, ascorbic acid, a-ketoglutaric acid and a-glycerophosphoric acid, the pH adjuster is used to adjust the pH of the aqueous solution for injection comprising the polyethylene glycol-modified camptothecin derivative to 3.0 to 4.0.

6. The pharmaceutical composition of claim 5, wherein the pH adjuster is one or a combination more than two selected from the group consisting of hydrochloric acid, acetic acid and phosphoric acid.

7. The pharmaceutical composition of claim 1, wherein in addition to the polyethylene glycol-modified camptothecin derivative, the pH adjuster and the water for injection, the components further comprises a lyophilized excipient.

8. The pharmaceutical composition of claim 7, wherein the lyophilized excipient is mannitol and/or lactose.

9. The pharmaceutical composition of claim 7, wherein the addition of the lyophilized excipient is 0 to 10% of the water for injection comprising the polyethylene glycol-modified camptothecin derivative by weight/volume ratio.

10. A preparation method of the pharmaceutical composition of the polyethylene glycol-modified camptothecin derivative of claim 1, comprising the following steps: (1) taking the polyethylene glycol-modified camptothecin derivative and adding a lyophilized excipient, adding water for injection with a total volume of water for injection in the composition of 70% to 90%, stirring to make the solution completely dissolved; (2) adjusting the pH to 3.0 to 4.0 with pH adjuster, adding water for injection to a full dose; (3) freeze-drying to obtain the product.

11. The preparation method of claim 10, wherein the total volume of the water for injection added into components in the step (1) is 90%; stirring in the step (1) is stirring to make the solution completely dissolved, and the pH is adjusted to 3.0 to 4.0 with the pH adjuster in the step (2), the temperature in the process of adding water for injection to the full dose is lower than 30° C.

* * * * *